(12) United States Patent
de Andrade et al.

(10) Patent No.: US 9,464,993 B1
(45) Date of Patent: Oct. 11, 2016

(54) METHOD AND APPARATUS FOR MEASUREMENT OF PHYSICAL PROPERTIES OF MATTER UNDER SIMULTANEOUS CONTROL OF RADIO FREQUENCY AND VARIABLE TEMPERATURES

(71) Applicant: The United States of America as represented by the Secretary of the Navy, Washington, DC (US)

(72) Inventors: Marcio C. de Andrade, San Diego, CA (US); Anna M. Leese de Escobar, Encinitas, CA (US)

(73) Assignee: The United States of America as represented by Secretary of the Navy, Washington, DC (US)

( * ) Notice: Subject to any disclaimer, the term of this patent is extended or adjusted under 35 U.S.C. 154(b) by 409 days.

(21) Appl. No.: 14/231,522

(22) Filed: Mar. 31, 2014

(51) Int. Cl.
*G01N 1/28* (2006.01)
*G01N 22/00* (2006.01)

(52) U.S. Cl.
CPC ................ *G01N 22/00* (2013.01); *G01N 1/28* (2013.01)

(58) Field of Classification Search
None
See application file for complete search history.

(56) References Cited

U.S. PATENT DOCUMENTS

| | | | |
|---|---|---|---|
| 4,012,954 A * | 3/1977 | Klippert | 73/150 R |
| 5,279,225 A | 1/1994 | Dow et al. | |
| 5,402,460 A * | 3/1995 | Johnson et al. | 378/10 |
| 7,013,742 B2 * | 3/2006 | Beraud | 73/865.6 |
| 2001/0003798 A1 | 6/2001 | McGovern et al. | |
| 2013/0015343 A1 | 1/2013 | Steiner et al. | |
| 2014/0328449 A1 * | 11/2014 | Nadeev et al. | 378/4 |

* cited by examiner

*Primary Examiner* — Robert R Raevis
(74) *Attorney, Agent, or Firm* — SPAWAR Systems Center Pacific; Kyle Eppele; J. Eric Anderson

(57) ABSTRACT

An apparatus allows a sample mounted within a temperature controlled radome system to be tested. The apparatus maintains the sample under controlled temperatures and allows radiation from a radiation source to expose the sample to broadband electromagnetic radiation of varying power, frequency and angle of incidence.

19 Claims, 3 Drawing Sheets

METHOD AND APPARATUS FOR MEASUREMENT OF PHYSICAL PROPERTIES OF MATTER UNDER SIMULTANEOUS CONTROL OF RADIO FREQUENCY AND VARIABLE TEMPERATURES

STATEMENT OF GOVERNMENT INTEREST

The United States Government has ownership rights in this invention. Licensing inquiries may be directed to Office of Research and Technical Applications, Space and Naval Warfare Systems Center, Pacific, Code 72120, San Diego, Calif., 92152; telephone (619)553-5118; email: ssc_pac_t2@navy.mil. Reference Navy Case No. #102193.

BACKGROUND OF THE INVENTION

In the fields of electronic surveillance, telecommunications, biology, medicine, and explosive devices, for example, there is a need to investigate the interaction of samples with electromagnetic radiation (EMR) at different frequencies and at different levels and directions while simultaneously exposing the samples to a controlled temperature environment. Such samples may include solid state devices, biological samples, and/or samples in liquid or gaseous state. The fundamental properties of a sample may depend on the temperature at which the sample is kept, the frequency of the electromagnetic wave that is incident to the sample, and the angle and power of the incident wave.

Some properties of electronic components can only be measured when the component is sufficiently cooled. For example, some electronic components are specifically designed to detect RF radiation but such detection is possible only when the component is adequately cool. Additionally, for example, some infrared sensors only work at low temperatures, as higher temperatures cause enough thermal noise to obscure sensing the signal of interest. Some biological samples, for example, may be easier to work with when cooled, as known levels of radiation are necessary to kill certain types of viruses or cells when the biological sample is cooled to a known temperature.

Thus, there is a need to investigate, characterize, and test samples when the samples are cooled to certain desired temperatures while the sample is simultaneously exposed at different angles and power of broadband electromagnetic energy ranging from DC to Tera-Hertz frequencies. There is also a need to measure the responses of a sample to incoming broadband EMR from DC to Tera-Hertz and to measure how the incident EMR alters the property and performance of the sample. There is, however, no current method for measuring a sample cooled, for example, from 3 Kelvin (K) up to 350 K, while the sample is exposed to electromagnetic radiation from DC to Tera-Hertz, in particular for wavelengths below infrared, commonly referred to as "the radio spectrum".

SUMMARY OF THE INVENTION

Some embodiments described herein provide an apparatus that includes a refrigeration system configured to provide controlled cooling to a sample and a connection interface configured to connect the refrigeration system with a radome system where the sample is placed. The radome system is configured to allow a radiation source to expose the sample to controlled and/or free space broadband electromagnetic radiation in various frequency ranges, to maintain the sample in a controlled temperature while the sample is exposed to the broadband electromagnetic radiation, and to be transparent to the broadband electromagnetic radiation directed to the sample.

Other objects, advantages and features will become apparent from the following detailed description when considered in conjunction with the accompanied drawings.

BRIEF DESCRIPTION OF THE DRAWINGS

The accompanying figures, where like reference numerals refer to identical or functionally similar elements throughout the separate views, together with the detailed description below, are incorporated in and form part of the specification, and serve to further illustrate embodiments of concepts that include the claimed invention, and explain various principles and advantages of those embodiments.

Figure 1:
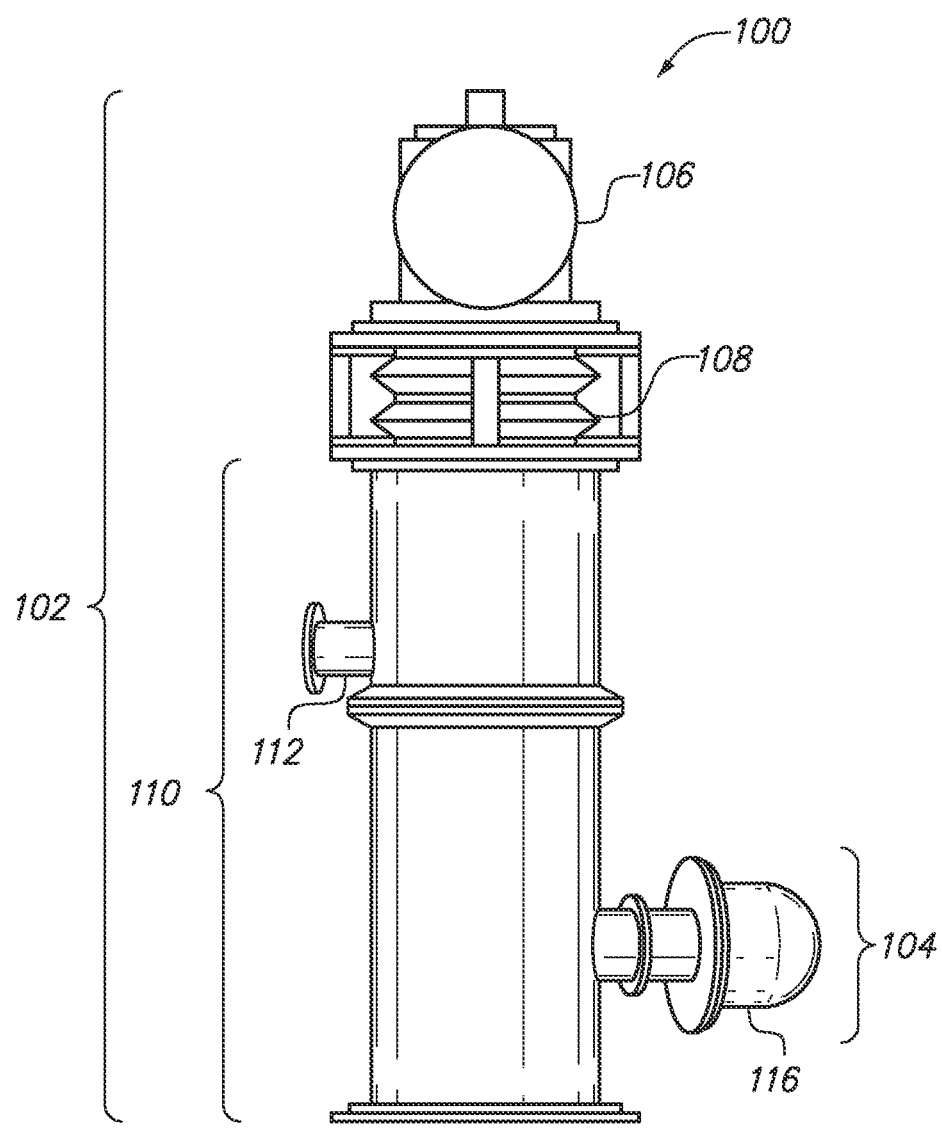
FIG. 1 is a diagram of a system according to the description herein.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

The apparatus and method components have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

DETAILED DESCRIPTION OF THE EMBODIMENTS

FIG. 1 is a diagram of a system 100 configured to allow broadband frequency measurements of samples. System 100, when used in conjunction with a source of radiation, is configured to expose samples to controlled and/or free-space electromagnetic radiation (EMR) in various frequency ranges that can be at near-field or far-field and beyond line-of-sight, while simultaneously maintaining the samples under controlled temperatures from, for example, 3 Kelvin (K) up to 350 K. The samples may be solid state devices, biological samples, and/or samples in liquid or gaseous state that are exposed to EMR from direct current (DC) up to Tera Hertz. System 100 is configured to permit frequency and direction controlled broadband EMR to be incident upon a sample enclosed within a temperature controlled environment.

System 100 includes a refrigeration system 102 and a radome system 104. Refrigeration system 102 provides a cold source to radome system 104 and may include a mechanical refrigeration system, for example, such as a cryocooler 106 that uses a vibration isolator 108 to isolate the vibrations of cryocooler 106 from a cryostat 110. Alternatively, cryocooler 106 and vibration damper 108 of refrigeration system 102 may be replaced with a reservoir of coolant such as liquid helium or a system that does not involve a coolant, such as adiabatic magnetization cooling utilizing the magneto-caloric effect.

Cryostat 110 is configured to maintain temperature control of a sample and keep a sample under a vacuum and/or controlled gas atmosphere. Diagnostic interface 112 is configured to allow electrical coupling to radome system 104 or to another component, such as a diagnostics component. System 100 may also include a response unit (not shown) to record responses from a sample exposed to different radiation frequencies while the sample is maintained under controlled temperatures.

As will be further explained, internal interfaces connect refrigeration system 102 to radome system 104 so that a sample placed within radome system 104 is within a controlled temperature environment. As can be seen, radome system 104 has an external radome 116 and an internal radome placed within external radome 116, to be further described.

Figure 2:
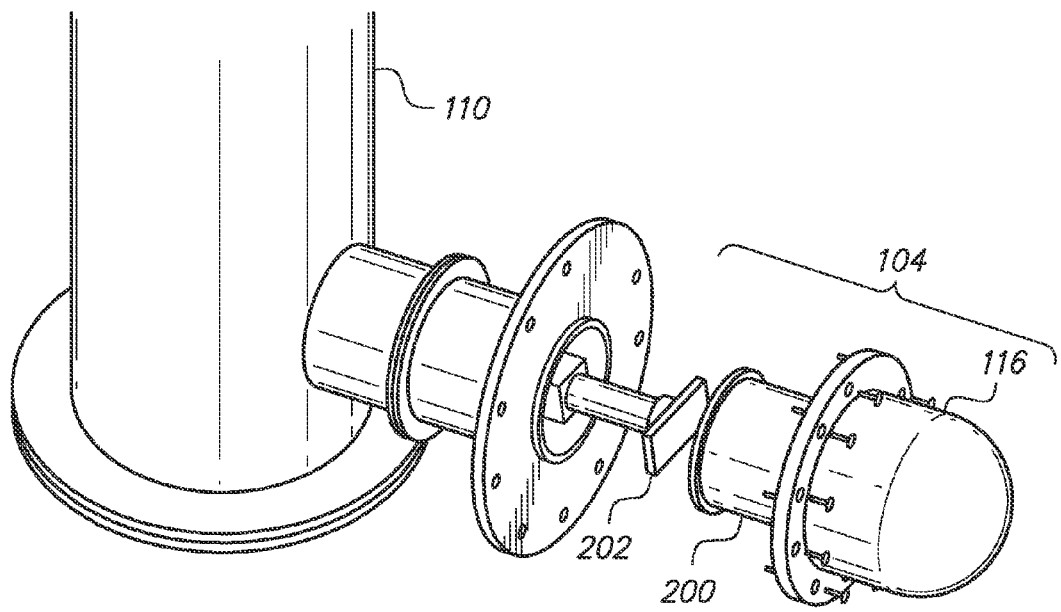
FIG. 2 is another diagram of a system according to the description herein.

FIG. 2 is a diagram that illustrates a portion of system 100 with external radome 116 and internal radome 200 being detached from cryostat 110 to reveal a sample holder 202. Wiring (not shown), connectors (not shown), supports (not shown), and sample holders, for example, sample holder 202, are designed to have a number of DC and radio frequency interconnects based on a design including printed circuit boards, RF connectors, and RF vias for control and readout lines with bandwidth from, for example, DC to above 5 GHz.

External radome 116 is made of a material that is substantially transparent to broadband electromagnetic radiation and is configured to maintain internal vacuum integrity of system 100. External radome 116 may be made of non-metallic materials, such as Teflon® or quartz. Internal radome 200 is also substantially transparent to broadband electromagnetic radiation and is of a non-metallic material with a high level of thermal conductivity, for example, ceramic Beryllium Oxide. As one skilled in the art will know, for either radome, the electromagnetic transparency of the material chosen will be contingent upon the choice of dielectric constant, loss tangent as well as other pertinent electrical parameters.

A cooling characteristic of cryostat 110 allows a first stage cooling aspect to be directed to internal radome 200. An internal interface of cryostat 110 interfaces directly with internal radome 200. The inherent thermal conductivity of the radome 200, in conjunction with a vacuum provided between inner radome 200 and outer radome 116, allows radome 200 to be cooled to a first stage cooling temperature, for example 40K.

In a mechanical refrigeration embodiment, helium gas is cycled in cryocooler 106 and the gas is condensed such that the resulting liquid helium bathes and cools down a sample holder 202 that is directly interfaced with a second stage cooling aspect of cryostat 110. Sample holder 202 is made of any suitable good thermal conductor such as copper, sapphire or beryllium oxide. As shown, sample holder 202 is designed to be inserted into the internal radome and is where samples to be tested are placed. Sample holder 202, as well as its accompanying sample, reaches a second stage cooling temperature lower that the first stage cooling temperature, for example a second stage cooling temperature of 4K. The sample placed in the internal radome may be mounted in vacuum or in gas and is vibration isolated or otherwise kept under mechanical isolation control. The internal radome is of a material that is a good thermal conductor but is also of a material designed to not influence on the electromagnetic waves being directed to the sample, such that any responses to the electromagnetic waves directed to the sample are from the sample itself and are not from the internal radome.

Radiation to the samples can be applied from any controlled or uncontrolled radiation source. For example, radiation can originate from a distant source and propagate through free space, or be applied from a controlled source such as a laser, fiber optics, or a transmission electromagnetic (TEM) cell. Controlled radiation may be directed to all or a portion of the sample being tested.

In addition to being a source of electromagnetic radiation, a TEM cell set at room temperature may be configured to control the power, amplitude and frequency of the incident electromagnetic waves. The TEM cell can also be rotated, from zero to 180 degrees, to provide different angles of arrival of the electromagnetic waves to the sample. According to one embodiment described herein, the TEM cell has an opening that allows radome system 104 to be inserted in it. The samples to be tested may be positioned at a "sweet spot" of the TEM cell, i.e., at a location in the center of the TEM cell where the incoming electromagnetic energy that propagates along the horizontal direction of the cell is spatially homogeneous and is controlled in frequency.

A response of interest from a sample may be maximized at a certain temperature, frequency, and incident angle and power of radiation. For example, the response of interest from a first sample may be maximized at 100 K and the response of interest from a second sample may be maximized at 50K. Thus, system 100 provides the ability for one to search for the temperature where the response of interest is maximized.

Figure 3:
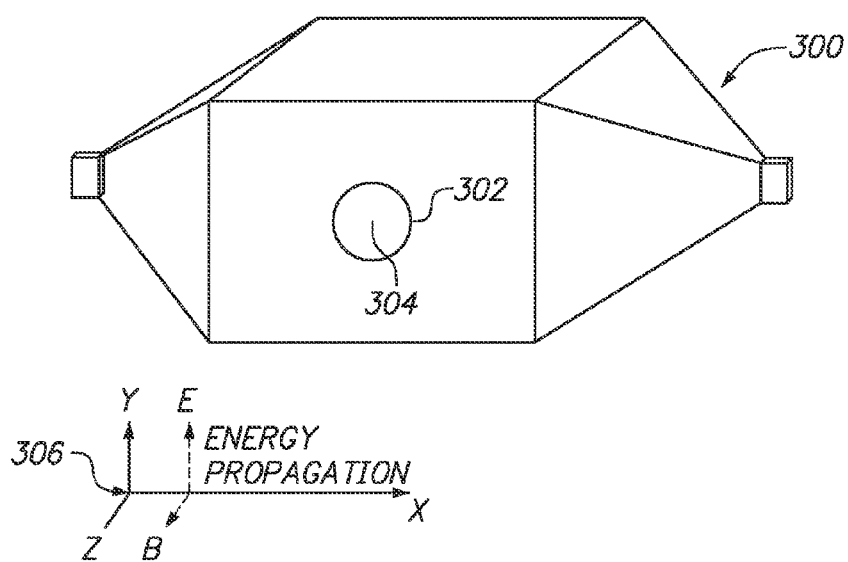
FIG. 3 is a diagram of a TEM cell as used in accordance with the description herein.

FIG. 3 is a diagram of a TEM cell used in accordance with some embodiments. TEM cell 300 has an opening 302 that allows for a radomed sample to be inserted in the TEM cell. Samples may be positioned to be tested at the center zone 304 of TEM cell 300 where the incoming electromagnetic energy 306 that propagates along the horizontal direction of the cell is spatially homogenous. The TEM cell can be used to control the frequency of the electromagnetic waves. The sample may also be set in relation to the incoming energy at different incidence angles by rotating TEM cell 300, for example, by means of an external platform and/or rotating the sample itself, such as, by means of a rotating mechanism attached to the sample holder. As the electromagnetic frequency, power, and angle, and the sample temperature are varied, it is possible to determine the response of a sample to a variety of conditions. The application of electromagnetic energy may be coherent or non-coherent and may be focused on the sample as a whole or any part thereof. The response of a sample may be recorded by monitoring changes in the sample's current, voltage, magnetic and/or optical properties, for example. Such changes may be observed via inductive measurements, for example.

Figure 4:
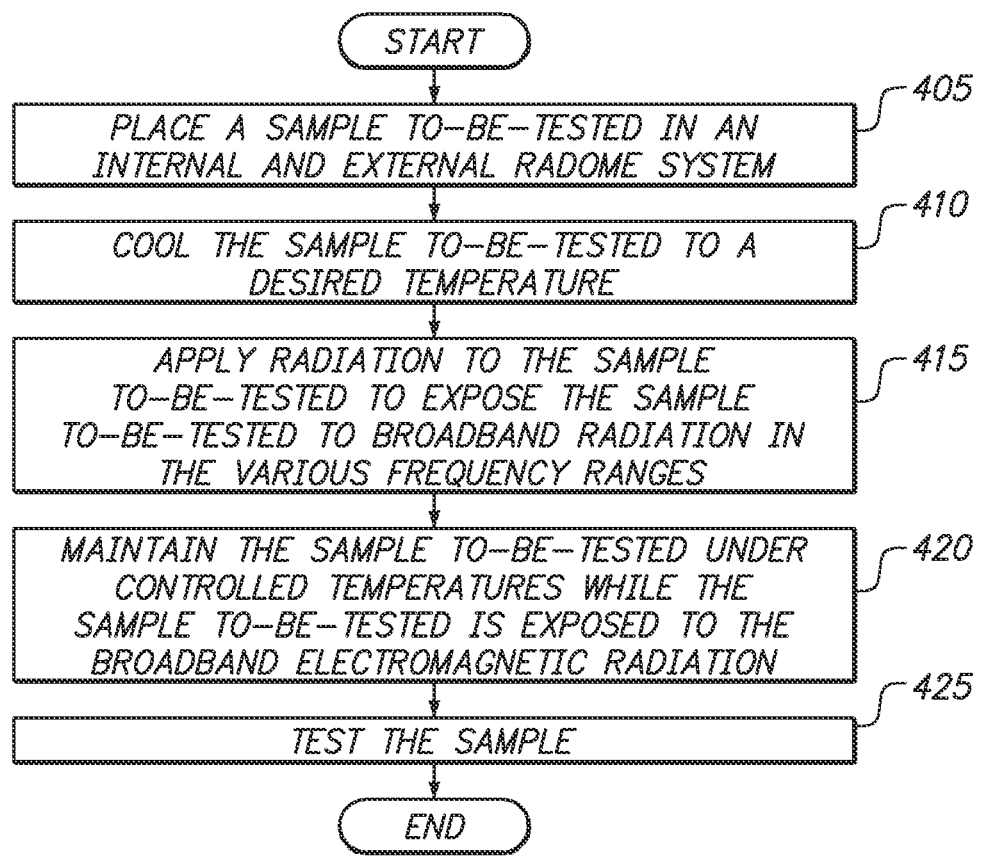
FIG. 4 is a flow diagram of steps as used in accordance with the description herein.

FIG. 4 is a flow diagram of the steps implemented in accordance with some embodiments. At 405, a sample is positioned on the sample holder located within the radome system's internal and external radomes. At 410, refrigeration of the sample takes place. For example, helium gas is condensed, by the mechanical refrigerator, such that the resulting helium liquid cools down a cryostat interface that makes mechanical contact to the sample holder where samples to be tested are positioned. At 415, radiation is applied to the sample from, for example, a transmission electromagnetic (TEM) cell or from radiation in free space. The TEM cell has an opening that allows for the radomed sample to be inserted in it. The sample may be positioned within the TEM cell where the incoming electromagnetic energy that propagates along the horizontal direction of the cell is spatially homogenous and the frequency of the electromagnetic waves can be finely controlled. The sample may also be oriented in relation to the incoming energy so as to receive the incoming energy at different incidence angles. At 420, the temperature environment of the sample is maintained while the sample is irradiated. At 425, testing of the sample involves exposing the sample to different electromagnetic frequencies, powers, and energy angles, as well as temperatures and recording the results.

It will be understood that many additional changes in the details, materials, steps and arrangement of parts, which have been herein described and illustrated to explain the nature of the invention, may be made by those skilled in the art within the principle and scope of the invention as expressed in the appended claims.

What is claimed is:

1. An apparatus comprising:
    a radiation source configured to direct radiation to a sample under test;
    a refrigeration system configured to provide a controlled temperature to the sample under test, wherein the refrigeration system includes:
        a cold source, and
        a cryostat operably coupled to the cold source, the cryostat being configured to maintain temperature control of the sample and to keep the sample under at least one of vacuum and controlled gas atmosphere; and
    a radome system where the sample under test is placed, wherein the radome system is configured to:
        allow electromagnetic radiation from the radiation source to be incident upon the sample,
        maintain the sample under the controlled temperature while the sample is exposed to the electromagnetic radiation, and
        be substantially transparent to the electromagnetic radiation directed to the sample.

2. The apparatus of claim 1, wherein the cold source is selected from the group consisting of a mechanical refrigeration system, an adiabatic magnet-caloric cooling system and liquid helium.

3. The apparatus of claim 1, wherein the radome system is configured to maintain vacuum integrity.

4. The apparatus of claim 1, further comprising a sample holder on which the sample is placed wherein the radome system includes a portion surrounding the sample holder which is made of a material that is a good thermal conductor.

5. The apparatus of claim 1, wherein the radiation source is selected from the group consisting of a controlled radiation source and an uncontrolled radiation source.

6. The apparatus of claim 1, wherein the radiation source is a transmission electromagnetic cell configured to control power, amplitude and frequency of electromagnetic waves directed to the sample and configured to be rotated to provide different angles of arrival of the electromagnetic waves to the sample.

7. The apparatus of claim 6, wherein the transmission electromagnetic cell includes an opening through which the radome system is inserted and wherein the sample placed in the radome system is exposed to electromagnetic energy that is spatially homogeneous.

8. The apparatus of claim 6, wherein the transmission electromagnetic cell includes an opening through which the radome system is inserted, wherein the sample placed in the radome system is oriented at different electromagnetic energy incidence angles by at least one of rotating the transmission electromagnetic cell and rotating the sample.

9. The apparatus of claim 1, wherein the controlled temperature ranges from 3 Kelvin (K) up to 350 K and the frequency range of the broadband electromagnetic radiation is from direct current (DC) to Tera Hertz.

10. The apparatus of claim 1, wherein the sample is selected from the group consisting of a solid state device, a biological sample, a sample in liquid state or a sample in gaseous state.

11. The apparatus of claim 1, further comprising a response unit configured to record responses from the sample to different radiation frequencies while the sample is maintained under controlled temperatures.

12. An apparatus comprising:
    a radiation source configured to direct radiation to a sample under test;
    a refrigeration system including
        a cold source;
        a cryostat operably coupled to the cold source and configured to maintain temperature control of a sample under test and to keep the sample under test under at least one of a vacuum and a controlled gas atmosphere;
    a radome system connected to the cryostat, wherein the radome system is configured to maintain vacuum integrity of the cryostat and is configured to conduct a first cryostat cooling temperature; and
        wherein the radome system includes a sample holder disposed therein, the sample holder configured to hold the sample to be tested and configured to conduct a second cryostat cooling temperature, wherein the radome system is configured to allow electromagnetic radiation from the radiation source to be incident upon the sample held by the sample holder.

13. The apparatus of claim 12, wherein the cold source is selected from the group consisting of a mechanical refrigeration system, an adiabatic magnet-caloric cooling system and liquid helium.

14. The apparatus of claim 12, wherein the sample placed in the internal radome is mounted in one of vacuum or gas.

15. The apparatus of claim 12, wherein the radiation source is a transmission electromagnetic cell configured to control power, amplitude and frequency of electromagnetic waves directed to the sample and configured to be rotated to provide different angles of arrival of the electromagnetic waves to the sample.

16. The apparatus of claim 15, wherein the transmission electromagnetic cell includes an opening through which the radome system is inserted, wherein the sample placed in the radome system is tested at a location in the center of the transmission electromagnetic cell where incoming electromagnetic energy that propagates along the horizontal direction of the transmission electromagnetic cell is spatially homogeneous.

17. The apparatus of claim 15, wherein the transmission electromagnetic cell includes an opening through which the radome system is inserted, wherein the sample placed in the radome system is set in relation to incoming energy at different incidence angles by at least one of rotating the transmission electromagnetic cell and rotating the sample.

18. A method comprising:
    placing a sample to be tested in a radome;
    cooling the sample to a desired temperature;
    applying electromagnetic radiation to the sample to be tested;

maintaining, by a cryostat connected to a cold source, the sample to be tested under controlled temperatures and keeping the sample to be tested under at least one of vacuum and controlled gas atmosphere while the sample to be tested is exposed to the electromagnetic radiation; and testing the sample.

19. The method of claim 18, further comprising maintaining vacuum integrity while the sample to be tested is exposed to the electromagnetic radiation.

\* \* \* \* \*